United States Patent
Tachikawa

(10) Patent No.: US 6,297,340 B1
(45) Date of Patent: Oct. 2, 2001

(54) METHOD FOR MANUFACTURING SILICON COMPOUND HAVING SUBSTITUENTS BONDED TO SILICON ATOMS VIA SI-C BONDS

(75) Inventor: Mamoru Tachikawa, Kanagawa (JP)

(73) Assignee: Dow Corning Asia, Ltd., Tokyo (JP)

( * ) Notice: Subject to any disclaimer, the term of this patent is extended or adjusted under 35 U.S.C. 154(b) by 0 days.

(21) Appl. No.: 09/604,356

(22) Filed: Jun. 27, 2000

(30) Foreign Application Priority Data

Jun. 21, 1999 (JP) .................................................. 11-174566

(51) Int. Cl.$^7$ ..................................................... C03G 77/08
(52) U.S. Cl. ........................... 528/15; 524/284; 524/157; 528/23; 528/25; 528/31; 556/412; 556/450; 556/479
(58) Field of Search ..................................... 556/479, 412, 556/450; 524/157, 284; 528/15, 31, 25, 23

(56) References Cited

U.S. PATENT DOCUMENTS

| | | | |
|---|---|---|---|
| 4,476,166 | * | 10/1984 | Eckberg . |
| 5,994,573 | * | 12/1998 | Tachikawa et al. . |
| 6,015,920 | * | 1/2000 | Schilling et al. . |
| 6,048,994 | * | 4/2000 | Tachikawa et al. . |
| 6,175,031 | * | 1/2001 | Tachikawa . |

\* cited by examiner

*Primary Examiner*—Margaret G. Moore
*Assistant Examiner*—Marc S. Zimmer
(74) *Attorney, Agent, or Firm*—Sharon K. Severance

(57) ABSTRACT

A hydrosilylation reaction method that achieves high catalytic activity and stability, and improves the positional selectivity of the hydrosilylation reaction product. The method comprises reacting an unsaturated compound selected from the group consisting of aromatic vinyl compounds and allyl halides with a silicon compound having hydrosilyl groups described by formula $HSiR_n(Z)_{3-n}$, where n=0, 1, or 2, R is a hydrocarbon group and Z is selected from the group consisting of a silamino group, siloxy group, and siloxanoxy group in the presence of a carboxylic acid compound, a silyl ester of a sulfonic acid, and a platinum catalyst.

11 Claims, No Drawings

METHOD FOR MANUFACTURING SILICON COMPOUND HAVING SUBSTITUENTS BONDED TO SILICON ATOMS VIA SI-C BONDS

BACKGROUND OF INVENTION

The present invention relates to a method for manufacturing a silicon compound having substituents bonded to silicon atoms via Si-C bonds by reacting an unsaturated compound and a silane compound for the purpose of improving physical properties and imparting reactivity.

The use of a hydrosilylation reaction is generally very effective in the chemical modification of organic compounds with silane compounds. A method that is used in this case involves a hydrosilylation reaction of an Si-H functional silane and an organic compound having unsaturated bonds. This method is applicable to quite a wide range of Si-H compounds and organic compounds having unsaturated bonds. A platinum or rhodium catalyst is generally used in the hydrosilylation reactions conducted industrially, but these metals are prohibitively expensive, and the catalytic efficiency of the hydrosilylation reaction is therefore of the utmost importance. Also, competing side reactions are frequently encountered with hydrosilylation reactions, and the hydrosilylation reaction itself includes reaction paths that produce a number of isomers. Therefore problems related to the catalyst, such as yield of the product, selectivity, and production of a single isomer, are always present in a hydrosilylation reaction. In an effort to reduce these problems modifications of the catalyst have been performed such as chemically bonding or adding various ligands to the catalyst or fixing the catalyst on various different carriers. In general, however, this chemical or physical modification has the problems that (1) the effect thereof is gradually lost and (2) the activity of a catalyst is generally lower the better its selectivity. Besides these problems, platinum catalysts slowly deactivate under oxygen-free conditions, and therefore the hydrosilylation reaction has to be conducted in the presence of oxygen, despite the fact that this leads to side reactions and poses a fire hazard.

It is an object of the present invention to provide a reaction method with which high catalytic activity and stability are realized and the positional selectivity of the hydrosilylation reaction product is enhanced in the hydrosilylation reaction of an organic compound having unsaturated groups and an H-Si functional silicon compound using a platinum catalyst. An objective is also to achieve these effects without adding any oxygen, and to reduce the danger of fire, explosion, and so on in a hydrosilylation reaction.

SUMMARY OF INVENTION

A hydrosilylation reaction method that achieves high catalytic activity and stability and improves the positional selectivity of the hydrosilylation reaction product. The method comprises reacting an unsaturated compound selected from the group consisting of aromatic vinyl compounds and allyl halides with a silicon compound having hydrosilyl groups described by formula $HSiR_n(Z)_{3-n}$, where n=0, 1, or 2, R is a hydrocarbon group, and Z is selected from the group consisting of a silamino group, siloxy group, and siloxanoxy group in the presence of a carboxylic acid compound, a silyl ester of a sulfonic acid, and a platinum catalyst.

DESCRIPTION OF INVENTION

The present invention is a method for manufacturing a silicon compound having substituents bonded to silicon atoms via Si-C bonds. The method comprises reacting (a) at least one unsaturated compound selected from the group consisting of aromatic vinyl compounds and allyl halides with (b) a silicon compound having hydrosilyl groups described by formula $$HSiR_n(Z)_{3-n} \tag{1}$$

where n is 0, 1, or 2; R is a hydrocarbon group; and Z is selected from the group consisting of silamino group, siloxy group, and siloxanoxy group; in the presence of (c) at least one carboxylic acid compound selected from the group consisting of (1) carboxylic acids,
(2) carboxylic anhydrides,
(3) silyl ester compounds of carboxylic acids described by formula

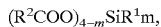

$$(R^2COO)_{4-m}SiR^1{}_m, \tag{2}$$

where m is an integer from 0 to 3; each $R^1$ is independently selected from the group consisting of $C_1$ to $C_6$ hydrocarbon groups and $C_1$ to $C_6$ alkoxy groups; and each $R^2$ group is independently selected from the group consisting of a hydrogen atom and $C_1$ to $C_{20}$ saturated or unsaturated hydrocarbon groups which may include at least one atom selected from among oxygen, halogens, sulfur, and silicon;

(d) a silyl ester of a sulfonic acid described by formula

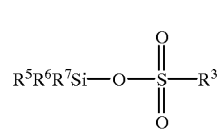

$$(3)$$

where $R^3$ is selected from the group consisting of $C_1$ to $C_{10}$ halogenated hydrocarbon groups, $C_1$ to $C_{10}$ alkyl groups, $C_6$ to $C_{10}$ aryl groups, a fluorine atom, a chlorine atom, a group described by formula $OR^4$, and a group described by formula $OSiR^8R^9R^{10}$; where $R^4$ is a $C_1$ to $C_6$ alkyl group; $R^8$, $R^9$, and $R^{10}$ are each independently selected from the group consisting of $C_1$ to $C_{10}$ hydrocarbon groups, $C_1$ to $C_{10}$ halogenated hydrocarbon groups, a halogen atom, and a hydrogen atom; and $R^5$, $R^6$, and $R^7$ are each independently selected from the group consisting of $C^1$ to $C_{10}$ hydrocarbon groups, a group described by formula $—OS(O_2)R^3$ where $R^3$ is as previously described, $C_1$ to $C_{10}$ halogenated hydrocarbon groups, a halogen atom, and a hydrogen atom; and (e) a platinum catalyst.

The above-mentioned aromatic vinyl compound refers to a compound in which at least one of the carbon atoms on the aromatic ring is bonded to a vinyl group (i.e. $—CH=CH_2$). Examples of this aromatic vinyl compound include styrene-based hydrocarbon compounds, such as p-methylstyrene, p-ethylstyrene, p-phenylstyrene, and divinylbenzene; halogen-containing styrenes, such as p-fluorostyrene, p-chlorostyrene, p-bromostyrene, p-iodostyrene, and p- and m-(chloromethyl)styrene; oxygen- or silicon-containing derivatives, such as p-methoxystyrene and p-trimethylsilylstyrene; and nitrogen-containing derivatives, such as p-(diphenylamino)styrene, p-(ditolylamino)styrene, p-(dixylylamino)styrene, and bis(4-vinylphenyl)(4methylphenyl)amine.

Specific examples of the above-mentioned allyl halides include allyl chloride and allyl bromide.

The above-mentioned silicon compound having hydrosilyl groups is described by formula (1) $HSiR_n(Z)_{3-n}$. In the formula R represents a hydrocarbon group, and is preferably selected from the group consisting of $C_1$ to $C_{10}$ alkyl groups, aryl groups, and aralkyl groups, such as the methyl group, ethyl group, propyl group, n-hexyl group, n-octyl group, cyclohexyl group, 2-ethylhexyl group, and other such saturated hydrocarbon groups; the phenyl group, tolyl group, xylyl group, and other such aryl groups; and the benzyl group, phenethyl group, and other such aralkyl groups. R is preferably a methyl group.

In the formula (1), Z is selected from the group consisting of silamino group, siloxy group, and siloxanoxy group. Specific examples thereof include —$OSiMe_2H$ (where Me is a methyl group and the same applies hereinafter), —$OSiMe_2OSiMe_2H$, —$OSiMe_2OSiMe_2OSiMe_2H$, —$OSiMe_3$, —$OSiMe_2OSiMe_3$, —$NHSiMe_3$, and —$NHSiMe2H$. Z may also be divalent rather than univalent and an example thereof is —OSiMeHOSiMeHOSiMeHO—.

The above-mentioned silicon compound having hydrosilyl groups preferably has 2 to 8 silicon atoms, specific examples of which include 1,1,3,3-tetramethyldisiloxane, 1,1,3,3,5,5-hexamethyltrisiloxane, 1,1,5,5-tetramethyl-3,3-diphenyltrisiloxane, 1,1,3,3,5,5,7,7-octamethyltetrasiloxane, $Si(—OSiMe2H)_4$, tetrakis(dimethylsiloxy)silane, and 3,3,5,5-tetrakis(dimethylsiloxy)-1,1,7,7-tetramethyltetrasiloxane.

The above-mentioned carboxylic acid compound is selected from among carboxylic acids described by the following formula 4, carboxylic anhydrides described by the following formula 5, and silyl ester compounds of carboxylic acids described by the following formula 2:

$$R^2COOH, \tag{4}$$

$$(R^2CO)_2O, \tag{5}$$

$$(R^2COO)_{4-m}SiR^1m, \tag{2}$$

where each $R^1$ is independently selected from the group consisting of $C_1$ to $C_6$ hydrocarbon groups and $C_1$ to $C_6$ alkoxy groups; each $R^2$ is independently selected from the group consisting of hydrogen atom $_1$ to $C_{20}$ saturated and unsaturated hydrocarbon groups which may include at least one atom selected from among oxygen, halogens, sulfur, and silicon; and m is an integer from 0 to 3

Examples of the above-mentioned carboxylic acid compound selected from among carboxylic acids, carboxylic anhydrides, and silyl esters of carboxylic acids include carboxylic acids such as formic acid, acetic acid, monochloroacetic acid, dichloroacetic acid, trichloroacetic acid, trifluoroacetic acid, propionic acid, acrylic acid, methacrylic acid, trimethylacetic acid, cyclohexanoic acid, lauric acid, stearic acid, benzoic acid, toluic acid, p-chlorobenzoic acid, terephthalic acid, and mesidinic acid; carboxylic anhydrides such as formic anhydride, acetic anhydride, propionic anhydride, butyric anhydride, lauric anhydride, stearic anhydride, phthalic anhydride, pyromellitic anhydride, and benzoic anhydride; and silyl esters of carboxylic acids such as esters of formic acid, including trimethylformyloxysilane, dimethylformyloxysilane, methyltriformyloxysilane, ethyltriformyloxysilane, phenyltriformyloxysilane, and tetraformyloxysilane; esters of acetic acid, including trimethylacetoxysilane, dimethylacetoxysilane, methyltriacetoxysilane, ethyltriacetoxysilane, phenyltriacetoxysilane, and tetraacetoxysilane; and esters of propionic acid, including trimethylpropionyloxysilane, dimethyldipropionyloxysilane, methyltripropionyloxysilane, methyldipropionyloxysilane, tripropionyloxysilane, ethyltripropionyloxysilane, phenyltripropionyloxysilane, and tetrapropionyloxysilane. The basic structure of the carboxylic acid may also be a dicarboxylic acid or a tricarboxylic acid.

Examples of the above-mentioned silyl ester of a sulfonic acid described by formula 3 include methanesulfonic acid silyl ester, ethanesulfonic acid silyl ester, benzenesulfonic acid silyl ester, toluenesulfonic acid silyl ester, trifluoromethanesulfonic acid silyl ester, fluorosulfuric acid silyl ester; chlorosulfuric acid silyl ester, sulfuric acid monoalkylmonosilyl ester, and sulfuric acid disilyl ester. Examples of the silyl groups in these esters include the trimethylsilyl group, triethylsilyl group, triisopropylsilyl group, and other such trialkylsilyl groups; the dimethylsilyl group, diethylsilyl group, diisopropylsilyl group, and other such dialkylsilyl groups; the dimethylphenylsilyl group, diethylphenylsilyl group, diisopropylphenylsilyl group, and other such dialkylarylsilyl groups; the dimethylchlorosilyl group, diethylchlorosilyl group, methyldichlorosilyl group, ethyldichlorosilyl group, and other such alkylchlorosilyl groups; and the dichlorosilyl group, trichlorosilyl group, and other such chlorosilyl groups.

The silyl ester of a sulfonic acid may also be a silyl ester in which a plurality of the above-mentioned sulfonic acid groups are bonded to a silicon. Examples of those in which two of the above-mentioned sulfonic acid groups are bonded include dimethylsilylene and methylchlorosilylene esters; examples of those in which three of the above-mentioned sulfonic acid groups are bonded include methylsilylene and chlorosilylene esters; and examples of those in which four of the above-mentioned sulfonic acid groups are bonded include silicon tetra(methanesulfonate) $(Si(CH_3SO_3)_4)$.

The compounding ratios of the above-mentioned components (a) to (e) as they participate in the reaction of the present invention will now be discussed.

The compounding ratio of the (a) unsaturated compound and (b) silicon compound having hydrosilyl groups is selected according to the desired product yield.

As to the amount in which the (c) carboxylic acid compound is compounded with respect to (a) unsaturated compound, it is recommended that the carboxylic acid compound be used such that the amount of acetoxy groups provided by the carboxylic acid compound is between 1 and 20 mol per 100 mol of the unsaturated groups provided by the unsaturated compound. The yield of the targeted product will decrease outside of this range.

As to the amount in which the (d) silyl ester of a sulfonic acid is added with respect to the (a) unsaturated compound, it is recommended that the silyl ester of a sulfonic acid be used in an amount of 0.01 to 1 mol per 100 mol of the unsaturated groups provided by the unsaturated compound (vinyl groups in the aromatic vinyl compound, or allyl groups in the allyl halide). The yield of the targeted product will decrease outside of this range.

There are no particular restrictions on the amount in which the (e) platinum catalyst is used, as long as it is sufficient for the hydrosilylation reaction to proceed, but an amount of 0.1 to 100 ppm with respect to the weight of the (a) unsaturated compound is favorable, for example, and a range of I to 10 ppm is preferable when reactivity and cost are factored in.

The reaction temperature should be at least 10° C. and no higher than 250° C., but from the standpoints of achieving a suitable reaction velocity and allowing the product and the substrate participating in the reaction to be stable, a temperature range of 20° C. to 200° C. is preferred.

The product obtained by the present method is a silicon compound having substituents bonded to silicon atoms via Si-C bonds, and more specifically is obtained by producing the above-mentioned Si-C bonds through an addition reaction between the hydrosilyl groups of the above-mentioned (b) silicon compound having hydrosilyl groups described by formula 1 and the vinyl groups of the above-mentioned (a) unsaturated compound.

When an aromatic vinyl compound is used as a raw material, the targeted product will be a compound having a structure in which a carbon atom in the beta position on the aromatic ring is directly bonded to a silicon atom originating in the above-mentioned (b) silicon compound having hydrosilyl groups described by formula 1. When an allyl halide is used as a raw material, however, the targeted product will be a compound having a structure in which a carbon atom at the end of the allyl group is directly bonded to a silicon atom originating in the above-mentioned (b) silicon compound having hydrosilyl groups described by formula 1.

The phrase "substituents bonded to silicon atoms via Si-C bonds" as used herein refers to an organic group bonded to a silicon atom through the above-mentioned addition reaction, and in the case of an aromatic vinyl compound this is the residue of the vinyl group after the addition reaction. For instance, in the case of styrene, this corresponds to a phenethyl group. In the case of an allyl halide, the above-mentioned substituent is the residue of the allyl group after the addition reaction, and in the case of allyl chloride, this corresponds to —$CH_2CH_2CH_2Cl$.

Specific examples of the catalyst used in the present invention include olefin complexes of zero-valent platinum, vinylsiloxane complexes of zero-valent platinum, olefin complex halides of divalent platinum, chloroplatinic acid, platinum carried on carbon, and platinum carried on silica, but this list is not comprehensive, and any other catalyst that is normally used industrially can be used.

EXAMPLES

The present invention will now be described in detail through working and comparative examples, but the present invention is not limited by these examples.

In the discussion of the characteristics of the product in the examples given below, GC stands for gas chromatography and GC-MS for gas chromatography-mass spectrometry, Me represents the methyl group, OAc the acetoxy group, and Ph the phenyl group.

The acyloxysilane compounds, alkylsilane compounds, and siloxane compounds used in these examples were commercially available or were synthesized by a known method. Commercially available unsaturated compounds were used without modification. The technology of this application will now be described by giving working and comparative examples.

Working Example 1

Reaction of styrene and 1,1,3,3-tetramethyldisiloxane with a platinum catalyst in the presence of trimethylacetoxysilane and a silyl ester of a sulfonic acid 380 mg Of styrene and 240 mg of 1,1,3,3-tetramethyldisiloxane were placed in a glass tube to which 20 μL (17.6 mg) of trimethylacetoxysilane ($Me_3SiOAc$) and 2 μL (2.3 mg) of triisopropylsilyl trifluoromethanesulfonate were added by microsyringe. 5 μL (platinum weight: 0.0017 mg) Of a toluene solution of zero-valent platinum complexed with divinylsiloxane were added to this. The tube was put in a 60° C. oil bath and heated for 8 hours. After cooling, the tube contents were analyzed by gas chromatography, which revealed that the styrene conversion rate was 96%, 1,3-bis(phenethyl)-1,1,3,3-tetramethyldisiloxane had been produced at a yield of 85%, and the ratio of alpha addition to beta addition of phenethyl groups was 1:15.9.

Comparative Example 1

Reaction of styrene and 1,1,3,3-tetramethyldisiloxane with a platinum catalyst (in the absence of a carboxylic acid compound and a silyl ester of a sulfonic acid)

520 mg Of styrene and 340 mg of 1,1,3,3-tetramethyldisiloxane were placed in a glass tube to which 10 μL (platinum weight: 0.0034 mg) of a toluene solution of zero-valent platinum complexed with divinylsiloxane were added. The tube was put in a 60° C. oil bath and heated for 2 hours. After cooling, the tube contents were analyzed by gas chromatography, which revealed that the styrene conversion rate was 98%, 1,3-bis(phenethyl)-1,1,3,3-tetramethyldisiloxane had been produced at a yield of 97%, and the ratio of alpha addition to beta addition of phenethyl groups was 1:2.8.

Comparative Example 2

Reaction of styrene and 1,1,3,3-tetramethyldisiloxane with a platinum catalyst in the presence of a carboxylic acid compound (in the absence of a silyl ester of a sulfonic acid)

380 mg Of styrene and 240 mg of 1,1,3,3-tetramethyldisiloxane were placed in a glass tube to which 20 μL of trimethylacetoxysilane ($Me_3SiOAc$) was added by microsyringe. 5 μL (platinum weight: 0.0017 mg) Of a toluene solution of zero-valent platinum complexed with divinylsiloxane were added to this. The tube was put in a 60° C. oil bath and heated for 8 hours. After cooling, the tube contents were analyzed by gas chromatography, which revealed that the styrene conversion rate was 99%, 1,3-bis(phenethyl)-1,1,3,3-tetramethyldisiloxane had been produced at a yield of 75%, and the ratio of alpha addition to beta addition of phenethyl groups was 1:3.1.

Comparative Example 3

Reaction of styrene and 1,1,3,3-tetramethyldisiloxane with a platinum catalyst in the presence of a silyl ester of a sulfonic acid (in the absence of a carboxylic acid compound)

520 mg Of styrene and 340 mg of 1,1,3,3-tetramethyldisiloxane were placed in a glass tube to which 2 μL (2.3 mg) of triisopropylsilyl trifluoromethanesulfonate (i-$Pr_3SiOSO_2CF_3$) were added by microsyringe. 10 μL (platinum weight: 0.0034 mg) Of a toluene solution of zero-valent platinum complexed with divinylsiloxane were added to this. The tube was put in a 60° C. oil bath and heated for 2 hours. After cooling, the tube contents were analyzed by gas chromatography, which revealed that the styrene conversion rate was 98%, 1,3-bis(phenethyl)-1,1,3, 3-tetramethyldisiloxane had been produced at a yield of 95%, and the ratio of alpha addition to beta addition of phenethyl groups was 1:3.0.

Working Example 2

Reaction of styrene and 1,1,3,3-tetramethyldisiloxane with a platinum catalyst in the presence of acetic anhydride and a silyl ester of a sulfonic acid 380 mg Of styrene and 240 mg of 1,1,3,3-tetramethyldisiloxane were placed in a glass tube to which 20 μL (21.6 mg) of acetic anhydride and 2 μL (2.3 mg) of triisopropylsilyl trifluoromethanesulfonate (i-Pr$_3$SiOSO$_2$CF$_3$) were added by microsyringe. 5 μL (platinum weight: 0.0017 mg) Of a toluene solution (platinum content: 0.04 wt %) of zero-valent platinum complexed with divinylsiloxane were added to this. The tube was put in a 60° C. oil bath and heated for 8 hours. After cooling, the tube contents were analyzed by gas chromatography, which revealed that the styrene conversion rate was 55%, 1-phenethyl-1,1,3,3-tetramethyldisiloxane had been produced at a yield of 58% (based on 1,1,3,3-tetramethyldisiloxane) and 1,3-bis(phenethyl)-1,1,3,3-tetramethyldisiloxane at a yield of 21%, and the ratio of alpha addition to beta addition of phenethyl groups was 1:49.

Comparative Example 4

Reaction of styrene and 1,1,3,3-tetramethyldisiloxane with a platinum catalyst in the presence of acetic anhydride (in the absence of a silyl ester of a sulfonic acid)

380 mg Of styrene and 240 mg of 1,1,3,3-tetramethyldisiloxane were placed in a glass tube to which 20 μL (21.6 mg) of acetic anhydride were added using a microsyringe. 5 μL (platinum weight: 0.0017 mg) Of a toluene solution of zero-valent platinum complexed with divinylsiloxane were added to this. The tube was put in a 60° C. oil bath and heated for 8 hours. After cooling, the tube contents were analyzed by gas chromatography, which revealed that the styrene conversion rate was 21%, 1-phenethyl-1,1,3,3-tetramethyldisiloxane had been produced at a yield of 31% (based on 1,1,3,3-tetramethyldisiloxane) and 1,3-bisphenethyl)- 1,1,3,3-tetramethyldisiloxane at a yield of 3%, and the ratio of alpha addition to beta addition of phenethyl groups was 1:5.0.

Working Example 3

Reaction of allyl chloride and 1,1,3,3-tetramethyldisiloxane with a platinum catalyst in the presence of ethyltriacetoxysilane and a silyl ester of a sulfonic acid 310 mg Of allyl chloride, 405 mg of 1,1,3,3-tetramethyldisiloxane, and 175 mg of toluene were placed in a glass tube to which 10 μL of ethyltriacetoxysilane (EtSi (OAc)$_3$) and 1 μL (1.15 mg) of triisopropylsilyl trifluoromethanesulfonate (i-Pr$_3$SiOSO$_2$CF$_3$) were added by microsyringe. 5 μL Of a toluene solution (platinum content: 0.04 wt %) of zero-valent platinum complexed with divinylsiloxane were added to this. The tube was put in an 80° C. oil bath and heated for 18 hours. After cooling, the tube contents were analyzed by gas chromatography, which revealed that 1-(γ-chloropropyl)-1,1,3,3-tetramethyldisiloxane had been produced at a yield of approximately 24%.

Comparative Example 5

Reaction of allyl chloride and 1,1,3,3-tetramethyldisiloxane with a platinum catalyst (in the absence of both a carboxylic acid compound and a silyl ester of a sulfonic acid)

310 mg Of allyl chloride, 405 mg of 1,1,3,3-tetramethyldisiloxane, and 175 mg of toluene were placed in a reaction tube to which 5 μL of a toluene solution (platinum content: 0.04 wt %) of zero-valent platinum complexed with divinylsiloxane were added. The tube was put in an 80° C. oil bath and heated for 18 hours. After cooling, the tube contents were analyzed by gas chromatography, which revealed that 1-(γ-chloropropyl)-1,1,3,3-tetramethyldisiloxane had been produced at a yield of approximately 11%.

Comparative Example 6

Reaction of allyl chloride and 1,1,3,3-tetramethyldisiloxane with a platinum catalyst in the presence of ethyltriacetoxysilane (in the absence a silyl ester of a sulfonic acid)

310 mg Of allyl chloride, 405 mg of 1,1,3,3-tetramethyldisiloxane, and 175 mg of toluene were placed in a glass tube, to which 10 μL of ethyltriacetoxysilane (EtSi (OAc)$_3$) were added by microsyringe. 5 μL Of a toluene solution (platinum content: 0.04 wt %) of zero-valent platinum complexed with divinylsiloxane were added to this. The tube was put in an 80° C. oil bath and heated for 18 hours. After cooling, the contents of the tube were analyzed by gas chromatography, which revealed that 1-(γ-chloropropyl)-1,1,3,3-tetramethyldisiloxane had been produced at a yield of approximately 9%.

Comparative Example 7

Reaction of allyl chloride and 1,1,3,3-tetramethyldisiloxane with a platinum catalyst in the presence of triisopropylsilyl trifluoromethanesulfonate (in the absence of a carboxylic acid compound 310 mg Of allyl chloride, 405 mg of 1,1,3,3-tetramethyldisiloxane, and 175 mg of toluene were placed in a glass reaction tube to which 1 μL of triisopropylsilyl trifluoromethanesulfonate (i-Pr$_3$SiOSO$_2$CF$_3$) was added by microsyringe. 5 μL Of a toluene solution (platinum content: 0.04 wt %) of zero-valent platinum complexed with divinylsiloxane were added to this. The tube was put in an 80° C. oil bath and heated for 18 hours. After cooling, the tube contents were analyzed by gas chromatography, which revealed that 1(γ-chloropropyl)-1,1,3,3-tetramethyldisiloxane had been produced at a yield of approximately 16%.

Comparative Example 8

Reaction of styrene and 1,1,3,3-tetramethyldisiloxane with a platinum catalyst in the presence of a carboxylic acid compound and trifluoroacetic acid (with a weak acid added instead of a silyl ester of a sulfonic acid)

380 mg of styrene and 240 mg of 1,1,3,3-tetramethyldisiloxane were placed in a glass tube, to which 20 μL of trimethylacetoxysilane (Me₃SiOAc) and 2 μL of trifluoroacetic acid were added by microsyringe. 5 μL Of a toluene solution (platinum content: 0.04 wt %) of zero-valent platinum complexed with divinylsiloxane were added to this. The tube was put in a 60° C. oil bath and heated for 8 hours. After cooling, the tube contents were analyzed by gas chromatography, which revealed that the styrene conversion rate was 99%, 1,3-bis(phenethyl)-1,1,3,3-tetramethyldisiloxane had been produced at a yield of 68%, and the ratio of alpha addition to beta addition of phenethyl groups was 1:3.9.

Working Example 4

Reaction of styrene and 1,1,3,3-tetramethyldisiloxane with a platinum catalyst in the presence of acetic acid and a silyl ester of a sulfonic acid 495 mg of styrene and 319 mg of 1,1,3,3-tetramethyldisiloxane were placed in a glass tube to which 10 μL of acetic acid and 2 μL of trimethylsilyl methanesulfonate (Me₃siOSO₂CH₃) were added by microsyringe. 5 μL Of a toluene solution (platinum content: 0.04 wt %) of zero-valent platinum complexed with divinylsiloxane were added to this. The tube was put in an 80° C. oil bath and heated for 5 hours. After cooling, the tube contents were analyzed by gas chromatography, which revealed that the styrene conversion rate was 98%, 1,3-bis(phenethyl)-1,1,3,3-tetramethyldisiloxane had been produced at a yield of 92%, and the ratio of alpha addition to beta addition of phenethyl groups was 1:11.2.

Comparative Example 9

Reaction of styrene and 1,1,3,3-tetramethyldisiloxane with a platinum catalyst (with only carboxylic acid compound added)

495 mg Of styrene and 319 mg of 1,1,3,3-tetramethyldisiloxane were placed in a glass tube to which 10 μL of acetic acid were added by microsyringe. 5 μL Of a toluene solution (platinum content: 0.04 wt %) of zero-valent platinum complexed with divinylsiloxane were added to this. The tube was put in an 80° C. oil bath and heated for 5 hours. After cooling, the tube contents were analyzed by gas chromatography, which revealed that the styrene conversion rate was 99%, 1,3-bis(phenethyl)-1,1,3,3-tetramethyldisiloxane had been produced at a yield of 94%, and the ratio of alpha addition to beta addition of phenethyl groups was 1:3.1.

I claim:

1. A method for manufacturing a silicon compound having substituents bonded to silicon atoms via Si-C bonds comprising reacting (a) an unsaturated compound selected from the group consisting of aromatic vinyl compounds and allyl halides with (b) a silicon compound having hydrosilyl groups described by formula

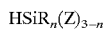

where n is 0, 1, or 2, R is a hydrocarbon group, and Z is selected from the group consisting of silamino group, siloxy group, and siloxanoxy group; in the presence of (c) a carboxylic acid compound selected from the group consisting of
   (1) carboxylic acids
   (2) carboxylic anhydrides
   (3) silyl ester compounds of carboxylic acids described by formula

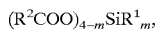

where m is an integer from 0 to 3, each $R^1$ is independently selected from the group consisting of $C_1$ to $C_6$ hydrocarbon groups and $C_1$ to $C_6$ alkoxy groups; and each $R^2$ is independently selected from the group consisting of a hydrogen atom and $C_1$ to $C_{20}$ saturated or unsaturated hydrocarbon groups which may including at least one atom selected from among oxygen, halogens, sulfur, and silicon;
   (d) a silyl ester of a sulfonic acid described by formula

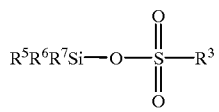

where $R^3$ is selected from the group consisting of $C_1$ to $C_{10}$ halogenated hydrocarbon groups, $C_1$ to $C_{10}$ alkyl groups, $C_6$ to $C_{10}$ aryl groups, a fluorine atom, a chlorine atom, a group described by formula $OR^4$, and a group described by formula $OSiR^8R^9R^{10}$; where, $R^4$ is a $C_1$ to $C_6$ alkyl group; $R^8$, $R^9$, and $R^{10}$ are each independently selected from a group consisting of $C_1$ to $C_{10}$ hydrocarbon groups, $C_1$ to $C_{10}$ halogenated hydrocarbon groups, a halogen atom, and a hydrogen atom; and $R^5$, $R^6$, and $R^7$ are each independently selected from a group consisting of $C_1$ to $C_{10}$ hydrocarbon groups, a group described by formula $—OS(O_2)R^3$, $C_1$ to $C_{10}$ halogenated hydrocarbon groups, a halogen atom, and a hydrogen atom; and
   (e) a platinum catalyst.

2. A method according to claim 1, where the unsaturated compound is an allyl halide selected from the group consisting of allyl chloride and allyl bromide.

3. A method according to claim 1, where R is methyl.

4. A method according to claim 1, where the silicon compound having hydrosilyl groups comprises 2 to 8 silicon atoms.

5. A method according to claim 1, where the carboxylic acid compound provides between 1 and 20 mol of acteoxy groups per 100 mol of unsaturated groups provided by the unsaturated compound.

6. A method according to claim 1, where the silyl ester of a sulfonic acid is added in an amount of 0.01 to 1 mol per 100 mol of unsaturated groups provided by the unsaturated compound.

7. A method according to claim 1, where the unsaturated compound is styrene.

8. A method according to claim 1, where the unsaturated compound is allyl chloride.

9. A method according to claim 1, where the silicon compound is 1,1,3,3-tetramethyldisiloxane.

10. A method according to claim 1, where the silyl ester of a sulfonic acid is selected from the group consisting of trimethylsilyl methanesulfonate and triisopropylsilyl trifluoromethanesulfonate.

11. A method according to claim 1, where the carboxylic acid compound is selected from the goup consisting of acetic acid, trimethylacetoxysilane, acetic anhydride, and ethyltriacetoxysilane.

* * * * *